United States Patent [19]

Ocel et al.

[11] 4,044,770

[45] Aug. 30, 1977

[54] EAR CURETTE

[75] Inventors: John J. Ocel; Donald J. Ocel; Jon A. Mathisrud, all of Minneapolis, Minn.

[73] Assignee: Ocelco, Inc., Minneapolis, Minn.

[21] Appl. No.: 565,003

[22] Filed: Apr. 4, 1975

[51] Int. Cl.² ............................................. A61B 17/22
[52] U.S. Cl. ................................................... 128/304
[58] Field of Search ........................................ 128/304

[56] References Cited

U.S. PATENT DOCUMENTS

| 1,737,106 | 11/1929 | Campbell et al. | 128/304 |
| 2,269,823 | 1/1942 | Kreiselman | 128/348 X |
| 2,617,420 | 11/1952 | Jozefczyk | 128/304 |
| 3,605,725 | 9/1971 | Bentov | 128/348 X |
| 3,630,190 | 12/1971 | Baker | 128/304 |
| 3,774,612 | 11/1973 | Marco | 128/304 |
| 3,955,579 | 5/1976 | Bridgman | 128/304 |

FOREIGN PATENT DOCUMENTS

| 674,469 | 4/1966 | Belgium | 128/304 |

Primary Examiner—Channing L. Pace
Attorney, Agent, or Firm—Orrin M. Haugen

[57] ABSTRACT

An ear curette which comprises, in combination, a generally resilient self-supporting flexible gripping shaft with a wire loop secured to the distal end thereof. The gripping shaft is fabricated from a substantially continuous solid shaft, with the distal end portion having a diameter which is significantly reduced from that of the proximal end segment so as to provide a generally rigid proximal end segment and a generally flexible distal end segment. Preferably, a tapered step is utilized to separate the proximal end from the distal end.

4 Claims, 5 Drawing Figures

EAR CURETTE

BACKGROUND OF THE INVENTION

The present invention relates generally to an ear curette means, and more specifially to an ear curette which has a flexible gripping shaft with a generally rigid proximal end segment, and a generally flexible distal end segment. The structure finds specific application as an ear currette device which permits the user to surgically scrape or clean the ear surface with controlled flexure of the gripping handle being possible.

In the past, ear curette devices have been fabricated from generally rigid materials such as stainless steel or the like. Flexibility, if at all available, is made available through only the wire loop portion only, and as such, provides limited flexural characteristics and utility for the overall structure. The present apparatus is designed to provide for flexure along a substantial portion of the gripping shaft, thereby enhancing the overall utility of the device by virtue of more precise control and manipulation of the gripping shaft.

SUMMARY OF THE INVENTION

Briefly, the ear curette means of the present invention utilizes the conventional gripping shaft with a wire loop means secured to the distal end thereof. More specifically, however, the gripping shaft is formed of a solid shaft or rod structure having a generally rigid proximal end segment and a generally flexible distal end segment, the differences in flexibility being achieved through a reduction of the diameter of the distal end segment. A tapered step or shoulder is provided for separating the distal end from the proximal end, with the tapered arrangement being utilized in order to avoid a concentration of stresses along a transverse plane of the shaft or rod.

Therefore, it is a primary object of the present invention to provide an improved ear curette means which comprises, in combination, a generally flexible gripping shaft with a wire loop means secured to the distal end thereof, and with the distal end segment of the gripping shaft being relatively flexible, and with the proximal end segment being relatively rigid.

It is yet a further object of the present invention to provide an improved ear curette means which includes a generally resilient self-supporting flexible gripping shaft with distal and proximal ends, and with the distal end being treated so as to be substantially more flexible than the proximal end.

It is still a further object of the present invention to provide an improved ear curette means which utilizes a generally solid flexible gripping shaft having a rigid proximal end segment and a generally flexible distal end segment, the two segments being separated, one from another, by a tapered step.

Other and further objects of the present invention will become apparent to those skilled in the art upon a study of the following specification, appended claims, and accompanying drawing.

DESCRIPTION OF THE PREFERRED EMBODIMENT

Figure 1:
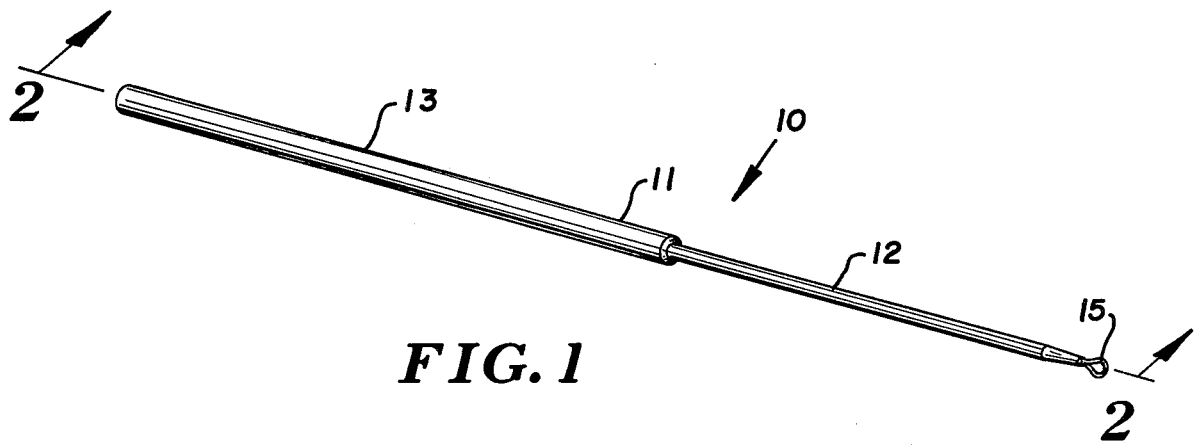
FIG. 1 is a perspective view of the ear curette means of the present invention and illustrating the arrangement of the proximal and distal segments.

In accordance with the preferred embodiment of the present invention, the ear curette means generally designated 10 includes a generally resilient self-supporting flexible gripping shaft 11 which includes a distal end segment 12 and a proximal end segment 13. As is apparent, the gripping shaft is a solid shaft or rod structure and the distal end segment is of significantly reduced diameter from that of the proximal end segment. At the distal tip, wire loop 15 is provided, with loop 15 having a pair of leg elements 16-16 disposed within the confines of bore 17 formed within the distal tip end. Preferably, bore 17 is arranged along the axis of the gripping shaft 11.

Figure 2:
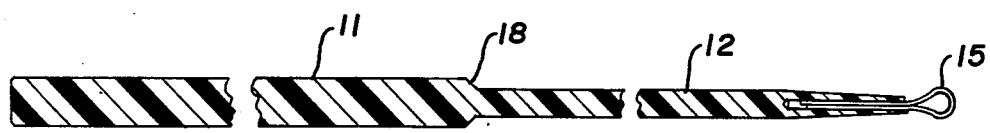
FIG. 2 is a sectional view taken through the diameter of the ear curette means as illustrated in FIG. 1, with a portion of the length of each of the distal and proximal segments being cut away from purposes of clarity.
Figure 3:
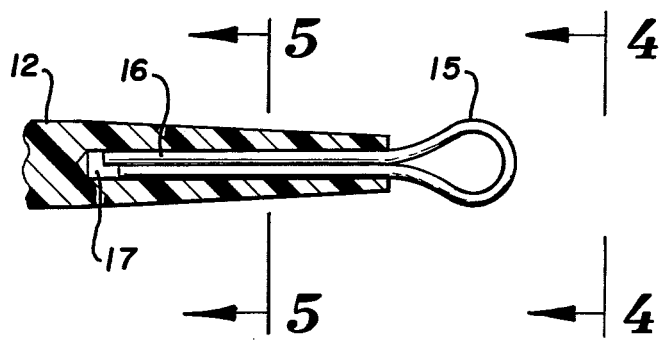
FIG. 3 is a partial sectional view taken through the diameter of the proximal tip portion, with this figure being on a slightly enlarged scale, and also illustrating the manner in which the wire loop means is received within the structure.
Figure 4:
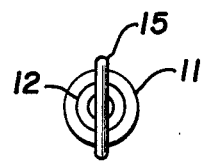
FIG. 4 is an end view of the device taken along the line and in the direction of the arrows 4—4 of FIG. 3.
Figure 5:
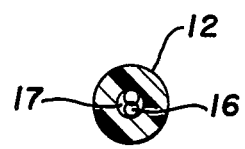
FIG. 5 is a sectional view taken along the line and in the direction of the arrows 5—5 of FIG. 3.

Separating the proximal end segment from the distal end segment is tapered step 18, as best illustrated in FIG. 2. The tapering step functions to distribute the radial stresses throughout a reasonable length of the gripping shaft, thereby avoiding areas of local fatigue, thus contributing to stability in the device.

As is expected, the wire loop means is preferably fabricated from a material acceptable for surgical procedures. Stainless steel may be utilized, as well as alternate materials such as stainless steel coated wire, brass wire, or the like.

The gripping shaft may be prepared from any durable material which is autoclavable. In this connection, nylon may qualify as well as molded polytetrafluoroethylene, with the latter material being available under the code name "Teflon" from E. I. DuPont deNemours Corp. of Wilmington, Del.

For most purposes, the wire loop will have a diameter of approximately 10 to 15 mils. The individual legs, for attachment purposes within the bore 17, should be approximately 1 inch in length.

As has been indicated, nylon is the preferred material for the gripping shaft. The overall length of the ear curette should be approximately 5 inches, with the diameter of the proximal portion being approximately 0.16 inch, and with the distal end having a diameter of approximately 0.09 inch. The tapered step is preferably a 45° step. If desired, the distal end may be tapered from an initial diameter of 0.09 inch at the step juncture to a tip diameter of about 0.06 inch. This provides a greater degree of flexibility for the tip portion and is, for that reason, preferred.

In order to achieve a desirable degree of flexibility in the curette, the following deflections are recommended:

| Weight Applied | Deflection |
| --- | --- |
| 15 grams | 6° |
| 30 grams | 12° |

-continued

| Weight Applied | Deflection |
| --- | --- |
| 50 grams | 19° |
| 75 grams | 28° |
| 100 grams | 35° |

The weight is applied to the wire loop portion at the tip, and the deflections are noted for the applied loads.

In connection with the deflection as occurs in response to applied loads, it will be appreciated that a deflection of about 35° is desirable with an applied load of between 75 grams and 125 grams.

As has been indicated, the distal end segment and proximal end segment each comprise approximately one-half of the total shaft length. For certain applications, particularly wherein the distal end segment is tapered, it may be possible to utilize a distal end portion which is slightly less than one-half of the overall length, with the length break-down of 2.3 inches for the distal end, and 3.86 inches for the proximal end segment.

The ear curette means of the present invention has been found to be exceptionally valuable in either disposable devices or devices retained for repeated usage.

We claim:

1. An ear curette means comprising, in combination, a generally resilient self-supporting flexible gripping shaft with distal and proximal ends and having a wire loop means secured to the distal end thereof, and wherein:
    a. said gripping shaft having a generally rigid proximal end segment and a generally flexible distal end segment and being a generally solid shaft with a certain first diameter at the proximal end segment and a certain reduced diameter at the distal end segment and with a tapered step separating said distal end from said proximal end to provide a generally rigid proximal end segment and a generally flexible distal end segment, and wherein a shaft deflection of 35° is achieved with a load of from between 75 and 125 grams secured to the tip end thereof.

2. The ear curette means as defined in claim 1 being particularly characterized in that said gripping shaft is fabricated from nylon and wherein said tapered step has an angle of 45°.

3. The ear curette means as defined in claim 1 being particularly characterized in that said generally solid shaft has a diameter ranging from between about 2 millimeters at the distal end and 4 millimeters at the proximal end.

4. The ear curette means as defined in claim 1 wherein said tapered step has an angle of 45°.

* * * * *